(12) United States Patent
Khapra et al.

(10) Patent No.: US 7,955,620 B2
(45) Date of Patent: Jun. 7, 2011

(54) STABLE ORAL COMPOSITION

(75) Inventors: Pankaj Khapra, Mumbai (IN); Nitin Bhalachandra Dharmadhikari, Mumbai (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 1294 days.

(21) Appl. No.: 10/583,842

(22) PCT Filed: Dec. 23, 2004

(86) PCT No.: PCT/IN2004/000399
§ 371 (c)(1), (2), (4) Date: Jun. 22, 2006

(87) PCT Pub. No.: WO2005/065047
PCT Pub. Date: Jul. 21, 2005

(65) Prior Publication Data
US 2007/0053974 A1 Mar. 8, 2007

(30) Foreign Application Priority Data
Dec. 23, 2003 (IN) .......................... 1304/MUM/2003

(51) Int. Cl.
*A61K 9/20* (2006.01)

(52) U.S. Cl. ........................................ 424/464; 514/290

(58) Field of Classification Search .................... 424/464
See application file for complete search history.

(56) References Cited

U.S. PATENT DOCUMENTS

| | | | |
|---|---|---|---|
| 6,100,274 A | 8/2000 | Kou | |
| 6,605,302 B2 * | 8/2003 | Faour et al. | 424/473 |
| 6,709,676 B2 * | 3/2004 | Cho | 424/472 |
| 7,175,854 B2 * | 2/2007 | Dietrich et al. | 424/464 |
| 2002/0123504 A1 | 9/2002 | Redmon et al. | |
| 2003/0031713 A1 | 2/2003 | Cho | |
| 2003/0118654 A1 | 6/2003 | Santos et al. | |
| 2003/0194430 A1 | 10/2003 | Miller et al. | |
| 2003/0236236 A1 | 12/2003 | Chen et al. | |

FOREIGN PATENT DOCUMENTS

| | | |
|---|---|---|
| CN | 1415613 | 5/2003 |
| CN | 1552324 A | 12/2004 |
| WO | 2004/080461 A2 | 9/2004 |
| WO | 2004/080461 A3 | 9/2004 |

* cited by examiner

*Primary Examiner* — Jake M. Vu
(74) *Attorney, Agent, or Firm* — Merchant & Gould P.C.

(57) ABSTRACT

The present invention provides a stable oral composition comprising a therapeutically effective amount of desloratadine and a stabilizer selected from the group comprising an antioxidant, a pharmaceutically acceptable organic compound that provides an alkaline pH, an alkali metal salt, or mixtures thereof, and pharmaceutically acceptable excipients.

7 Claims, No Drawings

STABLE ORAL COMPOSITION

The present invention relates to a solid oral pharmaceutical composition. More specifically this invention relates to a stable oral composition of descarbonylethoxyloratadine (Desloratadine).

BACKGROUND OF THE INVENTION

Descarbonylethoxyloratadine, also called desloratadine, is chemically known as 8-chloro-6,11-dihydro-11-(4-piperidylidene)-5H-benzo[5,6]-cyclohepta[1,2-b]pyridine. Desloratadine, a metabolic derivative of loratadine, is a long-acting tricyclic histamine antagonist with selective $H_1$-receptor histamine antagonist activity. Descarbonylethoxyloratadine is indicated for the relief of the nasal and non-nasal symptoms of allergic rhinitis (seasonal and perennial) in patients 12 years of age and older. It is also indicated for the symptomatic relief of pruritus, reduction in the number of hives, and size of hives, in patients with chronic idiopathic urticaria, 12 years of age and older.

U.S. Pat. No. 6,100,274 claims a stable pharmaceutical composition of desloratadine comprising a desloratadine-protective amount of a pharmaceutically acceptable basic salt and at least one pharmaceutically acceptable disintegrant. The patent mentions that acidic excipients discolor and decompose desloratadine. Desloratadine compositions were found to discolor when stored at 75% relative humidity ("RH") and a temperature of 40° C., alone or in combination with various excipients. This color instability in the active ingredient was attributed to a very minute amount of degradation product, the N-formyl impurity of desloratidine, which is formed due to the presence of a wide variety of excipients commonly used in oral formulations—especially tablet formulations. The unsuitable excipients include acidic excipients including, but not limited to, stearic acid, povidone and crospovidone, and other acidic excipients having a pH of less than 7 in water, preferably in the range of about 3 to 5, as well as excipients such as lactose, lactose monohydrate, sodium benzoate, and the like. The patent teaches the use of calcium, magnesium and aluminum salts of carbonates, phosphates, silicates and sulfates, or mixtures thereof as stabilizers. However, the patent does not teach any other means of stabilizing desloratadine.

United States Patent Application Number 20020123504A1 relates to stable pharmaceutical compositions of desloratadine formulated to avoid the incompatibility between desloratadine and reactive excipients such as lactose and other mono- and di-saccharides. Disclosed compositions include lactose-free, non-hygroscopic and anhydrous stable pharmaceutical compositions of desloratadine. The patent application teaches that stable composition of desloratadine can be obtained by using anhydrous process and excipients, such that the unbound water that may be present in the formulation is insufficient to initiate and/or accelerate any reaction of desloratadine with reactive excipients. Other means of stabilization taught by the patent application include coating of desloratadine particles to avoid contact with reactive excipients, or using large particles of desloratadine, so that surface area of contact with the reactive excipients is reduced. However, the methods suggested in this application either provide solutions that involve avoiding conventional formulation procedures such as wet granulation, or suggest other means that may affect bioavailability of the formulation, for example, coating or using large particles.

OBJECTS OF THE INVENTION

It is an object of the present invention to provide a stable pharmaceutical composition of desloratadine.

It is another object of the present invention to find novel means for stabilizing desloratadine compositions.

It is yet another object of the present invention to prevent or decrease the formation of N-formyl impurity in desloratadine composition, using novel means of stabilization.

It is still another object of the present invention to provide a pharmaceutical composition for desloratadine, which composition is stable in the presence of reactive excipients.

SUMMARY OF THE INVENTION

We have surprisingly found that pharmaceutical compositions comprising desloratadine can be stabilized using a stabilizer selected from the group comprising of an antioxidant, a pharmaceutically acceptable organic compound that provides an alkaline pH, an alkali metal salt and mixtures thereof. Hence, the invention lies in the use of a stabilizer, which stabilizer provides stability, while providing the freedom to use conventional excipients and processes. We have also surprisingly found that alkali metal salts functions as an effective stabilizer in pharmaceutical composition of desloratadine when used in small quantities whereas the basic salts used in prior art compositions are used in comparatively larger quantities.

Accordingly, the present invention provides a stable oral composition comprising desloratadine and a stabilizer selected from an antioxidant, a pharmaceutically acceptable organic compound that provides an alkaline pH, an alkali metal salt, and mixtures thereof, and pharmaceutically acceptable excipients.

DETAILED DESCRIPTION OF THE PRESENT INVENTION

The present invention provides a pharmaceutical compositions comprising desloratadine, a stabilizer selected from the group comprising an antioxidant, a pharmaceutically acceptable organic compound that provides an alkaline pH, an alkali metal salt and mixtures thereof, and pharmaceutically acceptable excipients.

The pharmaceutical composition of the present invention comprises desloratadine in a therapeutically effective amount. The term "therapeutically effective amount" as used herein indicates the amount of desloratadine required to be administered to a subject in need thereof, to have the desired therapeutic effect. In accordance with the present invention, desloratadine is preferably used in an amount ranging from about 0.1 mg to about 15 mg.

Compositions comprising desloratadine are known to be susceptible to chemical and physical degradation. Desloratadine is known to convert to N-formyl desloratadine impurity. Desloratadine is also known to undergo physical degradation such that the dosage forms comprising the drug turn pink in color. We have now found that stable oral compositions comprising desloratadine can be obtained using stabilizers, wherein the stabilizer is used in an amount such that it prevents discoloration of the composition, or prevents increase in the amount of the N-formyl desloratadine impurity above 0.5%, or both, when the composition is stored at 40° C. and 75% relative humidity over extended period of time. Preferably, the amount of stabilizer prevents discoloration of the composition or prevents increase in N-formyl desloratadine impurity above 0.5% or both, when the composition is stored at 40° C. and 75% relative humidity for 1 month. More preferably, the amount of stabilizer prevents discoloration of the composition or prevents increase in N-formyl desloratadine impurity above 0.5% or both, when the composition is stored at 40° C. and 75% relative humidity for 2 months. Still more preferably, the amount of stabilizer prevents discoloration of the composition or prevents increase in N-formyl desloratadine impurity above 0.5% or both, when the composition is stored at 40° C. and 75% relative humidity for 3 months. The compositions of the present invention are found to be stable when stored at 40° C. and 75% relative humidity for 3 months, which storage condition is indicative of the stability of the product when stored at ambient conditions for 24 months, i.e. the shelf life of the composition.

In one embodiment of the present invention, a stable oral composition of desloratadine is obtained using an antioxidant as a stabilizer. The antioxidants used in the present invention may be selected from the group consisting of butylated hydroxytoluene, butylated hydroxyanisole, DL-alpha-tocopherol, propyl gallate, octyl gallate, ethylenediamine tetraacetate, ascorbyl palmitate, acetyl cysteine, ascorbic acid, sodium ascorbate, fumaric acid, lecithin and the like and mixtures thereof. The antioxidants may be used in an amount ranging from about 0.01% to about 5% by weight of the composition.

In one embodiment of the present invention, a stable oral composition of desloratadine is obtained using as a stabilizer, a pharmaceutically acceptable organic compound that provides an alkaline pH. The pharmaceutically acceptable organic compound used in the present invention to provide an alkaline pH may be selected from the group consisting of primary, secondary and tertiary amines, cyclic amines, N,N'-dibenzylethylenediamine, diethanolamine, ethylenediamine, meglumine (N-methylglucamine), monosodium glutamate, polacrillin sodium, sodium alginate, and mixtures thereof. The organic compound may be used in an amount ranging from about 0.01% to about 5% by weight of the composition.

In one embodiment of the present invention, a stable oral composition of desloratadine is obtained using as a stabilizer, a pharmaceutically acceptable organic compound that provides an alkaline pH. The pharmaceutically acceptable organic compound used in the present invention to provide an alkaline pH may be selected from the group consisting of
  primary, secondary and tertiary amines, cyclic amines such as, N,N'-dibenzylethylenediamine, diethanolamine, ethylenediamine, meglumine (N-methylglucamine),
  monosodium glutamate,
  polacrillin sodium,
  sodium alginate, and
  mixtures thereof.

The organic compound may be used in an amount ranging from about 0.01% to about 5% by weight of the composition.

In one embodiment of the present invention, a stable oral composition of desloratadine is obtained using an alkali metal salt as a stabilizer. We have found that the alkali metal salts used in the present invention effectively stabilize the composition when used in smaller quantities than the alkaline earth metal salts that are used in the prior art compositions. Alkali-metal salts that may be preferably used include sodium and potassium salts of carbonates, phosphates, silicates, sulfates, citrates and the like and mixtures thereof. The alkali metal salt may be used in an amount ranging from about 0.01% to about 10% by weight of the composition.

The pharmaceutical composition of the present invention may further comprise inert pharmaceutically acceptable excipients such as diluents, flavoring agents, solubilizers, lubricants, suspending agents, binders, tablet disintegration agents or encapsulating materials. These excipients may be used in amounts conventional in the art.

The disintegrants used in the present invention may be selected from the group consisting of microcrystalline cellulose, starch, e.g., pregelatinized starch and corn starch, croscarmellose sodium and confectioner's sugar (a mixture of at least 95% by weight sucrose and corn starch that has been ground to a fine powder).

The binders used in the present invention may be selected from the group consisting of starch, gelatin, dextrin, maltodextrin, natural and synthetic gums like acacia, alginic acid, sodium alginate, guar gum, extract of Irish moss, ghatti gum, mucilage of isapol husks, carboxymethylcellulose, methylcellulose, hydroxyethyl cellulose, hydroxypropyl cellulose, hydroxypropyl methylcellulose, polyvinylpyrrolidone, veegum, arabogalactan and the like and mixtures thereof.

The lubricants used in the present invention may be selected from the group consisting of talc, magnesium stearate, calcium stearate, stearic acid, hydrogenated vegetable oils, polyethylene glycol and the like and mixtures thereof.

The typical glidants that may be included in the present invention include colloidal silicon dioxide, talc and the like.

Examples of wicking agents that may be used in the present invention include colloidal silicon dioxide, kaolin, titanium dioxide, fumed silicon dioxide, niacinamide, sodium lauryl sulfate, m-pyrol, vinylpyrrolidone polymers such as povidone, or crosslinked polyvinylpyrrolidone such as crospovidone; cellulose and cellulose derivatives such as microcrystalline cellulose, methylcellulose, ethylcellulose, hydroxypropylcellulose, hydroxypropyl cellulose, carboxyalkyl celluloses or crosslinked carboxyalkylcelluloses and their alkali salts; sodium starch glycolate, starch and starch derivatives, ion-exchange resins and the like and mixtures thereof.

The present invention may also include various other pharmaceutically acceptable excipients such as sweetening agents, wetting agents, flavoring agents, coloring agents and other such excipients.

The term "pharmaceutical composition" as used herein includes solid oral dosage forms such as pellets, beads, granules and the like, which may be encapsulated or compressed into tablets. The pellets, beads, granules in turn may be prepared by conventional methods known to a person skilled in the art. The compressed tablets may optionally be coated with film-coat.

The pharmaceutical composition of the present invention may be prepared by the conventional process of wet granulation, dry granulation or direct compression. In wet granulation, the drug along with the stabilizer and various excipients is mixed, granulated, followed by screening and drying of the damp mass. The dried mass may be screened, lubricated and compressed. Dry granulation can be done by two processes: (1) slugging, which involves mixing the drug with the stabilizer and the excipients, slugging, dry screening, lubrication and compression, and (2) roller compaction process. Direct compression involves compressing tablets directly from the powdered material of the drug, the stabilizer and the excipients.

Alternatively the pharmaceutical compositions of the present invention may be obtained by preparing placebo granules comprising the stabilizer and pharmaceutically acceptable excipients, and mixing these with desloratadine to obtain a blend, which may be encapsulated or compressed into tablets. This method provides compositions of desloratadine that are stable i.e. stable as regards chemical and physical degradation.

The examples that follow do not limit the scope of the invention and are merely used as illustrations.

EXAMPLE 1

The oral pharmaceutical composition of the present invention was obtained as per the formula given in Table 1 below.

This illustration exemplifies the use of a mixture of an antioxidant and a pharmaceutically acceptable organic compound that provides an alkaline pH, as a stabilizer.

TABLE 1

| Ingredients | Quantity | |
| --- | --- | --- |
| | mg/tablet | Percent weight by weight |
| Desloratadine | 5.0 | 5.0 |
| Butylated hydroxytoluene | 0.1 | 0.1 |
| Meglumine | 1.0 (in water) | 1.0 |
| Microcrystalline cellulose (Avicel PH 101) | 30.0 | 30.0 |
| Starch 1500 | 15.0 | 15.0 |
| Corn Starch Purity 21A | 36.9 | 36.9 |
| Microcrystalline cellulose (Avicel PH 102) | 10.0 | 10.0 |
| Talc | 2.0 | 2.0 |
| Average weight | 100.0 | 100.0 |

The butylated hydroxytoluene was dissolved in isopropyl alcohol. The desloratadine was granulated with the butylated hydroxytoluene solution and the granules were then dried (Stage I granules). Microcrystalline cellulose (Avicel PH 101), corn starch Purity 21 A and starch 1500 were mixed and granulated using meglumine solution in water. These granules were dried (Stage II granules). The Stage I granules and Stage II granules were mixed and lubricated with Avicel PH 102 and talc and compressed into tablets. The tablets were coated with aqueous coating dispersion.

The tablets thus obtained were subjected to dissolution testing using United States Pharmacopoeia type II dissolution apparatus at 50 rpm at 37±0.5° C. The dissolution medium used was 500 ml of 0.1N HCl. The results of the dissolution test are mentioned in Table 2 below.

TABLE 2

| Time (mins) | Percent drug released |
| --- | --- |
| 0 | 0 |
| 10 | 84 |
| 20 | 89 |
| 30 | 92 |
| 45 | 97 |

The tablets prepared were subjected to stability studies. The results of the stability study are given below in Table 3.

TABLE 3

| Stability condition 3 Months at 40 ± 2° C. and 75 ± 5% RH | |
| --- | --- |
| N-formyl desloratadin impurity | 0.07% |
| Description | No change in color of the tablet |

EXAMPLE 2

The oral pharmaceutical composition of the present invention was obtained as per the formula given in Table 4 below. The following illustration exemplifies the use of a pharmaceutically acceptable organic compound that provides an alkaline pH as a stabilizer.

TABLE 4

| Ingredients | Quantity | |
| --- | --- | --- |
| | mg/tablet | Percent weight by weight |
| Desloratadine | 5.0 | 5.0 |
| Meglumine | 1.0 (in water) | 1.0 |
| Microcrystalline cellulose (Avicel PH 101) | 30.0 | 30.0 |
| Starch 1500 | 15.0 | 15.0 |
| Corn Starch Purity 21A | 37.0 | 37.0 |
| Microcrystalline cellulose (Avicel PH 102) | 10.0 | 10.0 |
| Talc | 2.0 | 2.0 |
| Average weight | 100.0 | 100.0 |

Desloratadine, Avicel PH 101, Corn Starch Purity 21 A and Starch 1500 were mixed. The dry mixture was granulated with Meglumine solution. The granules were dried, lubricated with Avicel PH 102 and Talc and compressed into tablets. The tablets were coated with aqueous coating dispersion.

The tablets prepared were subjected to stability studies. The results of the stability study are given below in table 5.

TABLE 5

| Stability condition 3 Months at 40 ± 2° C. and 75 ± 5% RH | |
| --- | --- |
| N-formyl desloratadin impurity | 0.09% |
| Description | No change in color of the tablet |

EXAMPLE 3

The oral pharmaceutical compositions of the invention were also obtained as per the Formula given in Table 6 and 8 below. The following illustration exemplifies the use of an antioxidant as a stabilizer.

TABLE 6

| Ingredients | Quantity | |
| --- | --- | --- |
| | mg/tablet | Percent weight by weight |
| Desloratadine | 5.0 | 5.0 |
| Butylated hydroxytoluene | 0.1 | 0.1 |
| Microcrystalline cellulose (Avicel PH 101) | 72.15 | 72.15 |
| Starch 1500 | 15.0 | 15.0 |
| Sodium starch glycolate | 4.0 | 4.0 |
| Colloidal silicon dioxide | 1.5 | 1.5 |
| Talc | 2.0 | 2.0 |
| Magnesium stearate | 0.25 | 0.25 |
| Average weight | 100.0 | 100.0 |

The butylated hydroxytoluene was dissolved in isopropyl alcohol. The desloratadine was granulated with the butylated hydroxytoluene solution. The granules were dried and mixed with Avicel PH 112, Starch 1500, Sodium Starch Glycolate, Colloidal Silicon Dioxide, talc and Magnesium Stearate and compressed into tablets. The tablets were coated with aqueous coating dispersion.

The tablets prepared were subjected to stability studies. The results of the stability study are given below in table 7.

TABLE 7

Stability condition
2 Months at 40 ± 2° C. and 75 ± 5% RH

| | |
|---|---|
| N-formyl desloratadin impurity | 0.13% |
| Description | No change in color of the tablet |

TABLE 8

| Ingredients | Quantity mg/tablet | Percent weight by weight |
|---|---|---|
| Desloratadine | 5.0 | 5.0 |
| Butylated hydroxytoluene | 0.1 | 0.1 |
| Microcrystalline cellulose (Avicel PH 101) | 30.0 | 30.0 |
| Starch 1500 | 15.0 | 15.0 |
| Corn Starch Purity 21A | 37.9 | 37.9 |
| Microcrystalline cellulose (Avicel PH 102) | 10.0 | 10.0 |
| Talc | 2.0 | 2.0 |
| Average weight | 100.0 | 100.0 |

The butylated hydroxytoluene was dissolved in isopropyl alcohol. The desloratadine was granulated with the butylated hydroxytoluene solution and the granules were dried. Avicel PH 101, Corn Starch Purity 21 A and Starch 1500 were mixed and granulated using water. The granules were then dried. These granules were mixed with the desloratadine granules, lubricated with Avicel PH 102 and Talc and compressed into tablets. The tablets were coated with aqueous coating dispersion.

The tablets prepared were subjected to stability studies. The results of the stability study are given below in table 9.

TABLE 9

Stability condition
3 Months at 40 ± 2° C. and 75 ± 5% RH

| | |
|---|---|
| N-formyl desloratadine impurity | 0.11% |
| Description | No change in color of the tablet |

EXAMPLE 4

The oral pharmaceutical composition of the present invention was also obtained as per the Formula given in Table 10 below. This illustration exemplifies the use of an alkali metal salt as a stabilizer.

TABLE 10

| Ingredients | Quantity mg/tablet | Percent weight by weight |
|---|---|---|
| Desloratadine | 5.0 | 5.0 |
| Corn starch | 40.0 | 40.0 |
| Pregelatinized starch | 12.5 | 12.5 |
| Microcrystalline cellulose(Avicel PH 101) | 25.0 | 25.0 |
| Disodium hydrogen phosphate | 0.5 | 0.5 |
| Starch pregelatinized | 5.0 | 5.0 |
| Microcrystalline cellulose(Avicel PH 112) | 9.0 | 9.0 |
| Talc | 3.0 | 3.0 |
| Opadry (aqueous dispersion) | 6.3% weight gain | |
| Average weight | 100.0 | 100.0 |

Corn starch, pregelatinized starch, microcrystalline cellulose and disodium hydrogen phosphate were mixed and granulated with water. The dried granules were blended with desloratadine, pregelatinized starch, microcrystalline cellulose and talc and tablets were compressed. The resultant tablets were coated with aqueous opadry dispersion.

The tablets prepared were subjected to stability studies. The results of the stability study are given below in table 11.

TABLE 11

Stability condition
1 Month at 40 ± 2° C. and 75 ± 5% RH

| | |
|---|---|
| N-formyl Desloratadine impurity | 0.02% |
| Description | No change in color of the tablet |

EXAMPLE 5

The oral pharmaceutical composition of the invention was also obtained as per the Formula given in Table 12 below. This illustration exemplifies the use of a pharmaceutically acceptable organic compound that provides an alkaline pH as a stabilizer.

TABLE 12

| Ingredients | Quantity mg/tablet | Percent weight by weight |
|---|---|---|
| Desloratadine | 5.051 | 5.051 |
| Corn starch | 20.0 | 20.0 |
| Pregelatinized starch | 15.0 | 15.0 |
| Microcrystalline cellulose(Avicel PH 101) | 23.4 | 23.4 |
| Meglumine | 0.5 | 0.5 |
| Pregelatinized starch | 10.0 | 10.0 |
| Butylated hydroxy toluene | 0.1 | 0.1 |
| Sodium starch glycolate | 4.0 | 4.0 |
| Microcrystalline cellulose (Avicel PH 112) | 19.949 | 19.949 |
| Talc | 2.0 | 2.0 |
| Opadry (aqueous dispersion) | 3.46% weight gain | |
| Average weight | 100.0 | 100.0 |

Corn starch, pregelatinized starch and microcrystalline cellulose were mixed and granulated with aqueous solution of meglumine. The granules were then dried. Pregelatinized starch was then granulated with solution of Butylated hydroxy toluene in isopropyl alcohol. The granules were then dried. Stage I and stage II granules were blended with desloratadine, sodium starch glycolate, microcrystalline cellulose and talc. The blend was compressed into tablets and then coated.

The tablets prepared were subjected to stability studies. The results of the stability study are given below in table 13.

TABLE 13

Stability condition
3 Months at 40 ± 2° C. and 75 ± 5% RH

| | |
|---|---|
| N-formyl Desloratadine impurity | 0.07% |
| Description | No change in color of the tablet |

EXAMPLE 6

The oral pharmaceutical composition of the invention was also obtained as per the Formula given in Table 14 below. This illustration exemplifies the use of a pharmaceutically acceptable organic compound that provides an alkaline pH as a stabilizer.

TABLE 14

| Ingredients | Quantity mg/tablet | Percent weight by weight |
|---|---|---|
| Desloratadine | 5.051 | 5.051 |
| Corn starch | 20.0 | 20.0 |
| Pregelatinized starch | 15.0 | 15.0 |
| Microcrystalline cellulose (Avicel PH 101) | 23.4 | 23.4 |
| Meglumine | 0.5 | 0.5 |
| Pregelatinized starch | 10.0 | 10.0 |
| Sodium starch glycolate | 4.0 | 4.0 |
| Microcrystalline cellulose (Avicel PH 112) | 19.949 | 19.949 |
| Sodium stearyl fumarate | 2.0 | 2.0 |
| Opadry (aqueous dispersion) | 3.5% weight gain | |
| Average weight | 100.0 | 100.0 |

Corn starch, pregelatinized starch and microcrystalline cellulose were mixed and granulated with aqueous solution of meglumine. The granules were then dried. The granules were then blended with pregelatinized starch, desloratadine, sodium starch glycolate, microcrystalline cellulose and sodium stearyl fumarate. The blend was compressed into tablet and then coated.

The tablets prepared were subjected to stability studies. The results of the stability study are given below in table 15.

TABLE 15

Stability condition
2 Months at 40 ± 2° C. and 75 ± 5% RH

| | |
|---|---|
| N-formyl Desloratadine impurity | 0.03% |
| Description | No change in color of the tablet |

COMPARATIVE EXAMPLE 1

Oral pharmaceutical composition of desloratadine comprising no stabilizer was prepared as per Formula given in Table 16 below.

TABLE 16

| Ingredients | Quantity mg/tablet | Percent weight by weight |
|---|---|---|
| Desloratadine | 5.0 | 5.0 |
| Microcrystalline cellulose (Avicel PH 101) | 30.0 | 30.0 |
| Starch 1500 | 15.0 | 15.0 |
| Corn Starch Purity 21A | 38.0 | 38.0 |
| Microcrystalline cellulose (Avicel PH 102) | 10.0 | 10.0 |
| Talc | 2.0 | 2.0 |
| Average weight | 100.0 | 100.0 |

Desloratadine, Avicel PH 101, Corn Starch Purity 21A and Starch 1500 were mixed and granulated using water. The granules were lubricated with Avicel PH 102 and Talc and compressed into tablets. The tablets were coated with aqueous coating dispersion.

The tablets prepared were subjected to stability studies. The results of the stability study are given below in table 17.

TABLE 17

Stability condition
3 Months at 40 ± 2° C. and 75 ± 5% RH

| | |
|---|---|
| N-formyl Desloratadine impurity | 0.19% |
| Description | Tablets turned light pink from initial white color |

COMPARATIVE EXAMPLE 2

Oral pharmaceutical composition of desloratadine comprising no stabilizer was also prepared as per the Formula given in Table 18 below.

TABLE 18

| Ingredients | Quantity mg/tablet | Percent weight by weight |
|---|---|---|
| Desloratadine | 5.0 | 4.90 |
| Lactose monohydrate | 32.0 | 31.38 |
| Microcrystalline cellulose (Avicel PH 101) | 46.5 | 45.60 |
| Pregelatinized starch | 10.0 | 9.81 |
| Sodium Starch glycolate | 4.0 | 3.92 |
| Talc | 0.75 | 0.74 |
| Colloidal silicon dioxide | 0.75 | 0.74 |
| Sodium stearyl fumarate | 1.0 | 0.98 |
| Opadry (readymix for coating) | 1.97 | 1.93 |

Desloratadine, lactose monohydrate, microcrystalline cellulose and pregelatinized starch were granulated with water and dried. Dried granules were mixed with sodium starch glycolate, talc, and sodium stearyl fumarate and compressed in to tablets. The tablets were then coated with aqueous opadry dispersion.

The tablets prepared were subjected to stability studies. The results of the stability study are given below in Table 19.

TABLE 19

Stability condition
1 Months at 40 ± 2° C. and 75 ± 5% RH

| | |
|---|---|
| N-formyl Desloratadine impurity | 0.24% |
| Description | Tablets turned light pink from initial white color |

COMPARATIVE EXAMPLE 3

Oral pharmaceutical composition of desloratadine comprising no stabilizer was also prepared as per the Formula given in Table 20 below.

TABLE 20

| Ingredients | Quantity mg/tablet | Percent weight by weight |
|---|---|---|
| Desloratadine | 5.0 | 4.90 |
| Xylitol, directly compressible (Xylitab 200) | 61.5 | 60.29 |
| Microcrystalline cellulose(Avicel PH 112) | 18.0 | 17.65 |
| Pregelatinized starch | 5.0 | 4.90 |
| Corn starch | 5.0 | 4.90 |
| Talc | 3.0 | 2.94 |
| Colloidal silicon dioxide | 1.0 | 0.98 |

TABLE 20-continued

| Ingredients | Quantity mg/tablet | Percent weight by weight |
|---|---|---|
| Magnesium stearate | 3.5 | 3.43 |
| Opadry ready mix for coating (non-aqueous coating dispersion) | qs | |
| Average weight | 102 | 100.0 |

The ingredients listed in the above table were blended and compressed into tablets. The tablets were then coated.

The tablets prepared were subjected to stability studies. The results of the stability study are given below in table 21 below.

TABLE 21

| Stability condition 2 Months at 40 ± 2° C. and 75 ± 5% RH | |
|---|---|
| N-formyl Desloratadine impurity | 1.20% |
| Description | Tablets turned light pink from initial white color |

The tablets of examples 1, 2, 3, 4, 5 and 6 were found to be stable, physically and chemically, as compared to the tablets of comparative example 1, 2 and 3.

While the invention has been described by reference to specific embodiments, this was done for purposes of illustration only and should not be construed to limit the spirit or the scope of the invention.

The invention claimed is:

1. A stable oral composition comprising a therapeutically effective amount of desloratadine, meglumine, and pharmaceutically acceptable excipient;
   wherein the desloratadine is stable to the extent that after 3 months at 40° C. and 75% relative humidity less than 0.5% w/w of the N-formyl impurity of desloratadine has formed.

2. The stable oral composition of claim 1, further comprising antioxidant.

3. The stable oral composition of claim 2, wherein the antioxidant comprises butylated hydroxytoluene.

4. The stable oral composition of claim 2, wherein the antioxidant is in an amount of about 0.01% to about 5% by weight of the composition.

5. The stable oral composition of claim 1, wherein meglumine is in an amount of about 0.01% to about 5% by weight of the composition.

6. The stable oral composition of claim 1, wherein the composition does not undergo discoloration, when stored at 40° C. and 75% relative humidity over a period of 3 months.

7. A stable oral composition comprising:
   a therapeutically effective amount of desloratadine,
   about 0.01% to about 5% by weight meglumine, and
   a pharmaceutically acceptable excipient;
   wherein the meglumine is effective stabilize the desloratadine to the extent that after 3 months at 40° C. and 75% relative humidity less than 0.5% w/w of the N-formyl impurity of desloratadine has formed.

* * * * *